__United States Patent__ [19]

Zabunova et al.

[11] Patent Number: 4,704,468
[45] Date of Patent: Nov. 3, 1987

[54] ESTERS OF O(2,6-DICHLOROPHENYLAMINO) PHENYLACETIC ACID

[75] Inventors: Orhideya B. Zabunova; Hristo B. Zvetanov; Lyudmila V. Petrova; Vaska A. Ognyanova; Milka P. Nikolova; Georgi L. Tanev; Nedyalka S. Ivanova, all of Sofia, Bulgaria

[73] Assignee: T P O "Pharmachim", Sofia, Bulgaria

[21] Appl. No.: 840,586

[22] Filed: Mar. 17, 1986

[51] Int. Cl.$^4$ ............................ C07C 101/447
[52] U.S. Cl. ........................ 560/43; 562/449
[58] Field of Search ................... 560/43; 562/449

[56] References Cited

U.S. PATENT DOCUMENTS

| | | | |
|---|---|---|---|
| 3,511,872 | 5/1970 | Sherlock | 560/47 X |
| 3,558,690 | 1/1971 | Sallmann et al. | 560/47 |
| 4,189,595 | 2/1980 | Sakoda et al. | 560/47 |
| 4,375,478 | 3/1983 | Horrom et al. | 560/47 X |
| 4,548,952 | 10/1985 | Casas | 514/533 |

Primary Examiner—Werren B. Lone
Assistant Examiner—Vera C. Clarke

[57] ABSTRACT

This invention relates to biologically active esters of 0(2,6-dichlorophenylamino) phenylacetic acid and a method for their preparation. The inventive esters have the formula

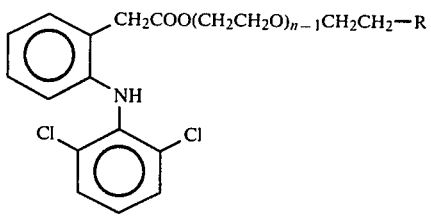

wherein R represents a hydroxyl group or the radical

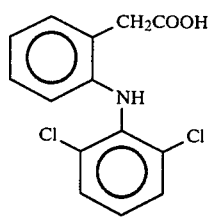

and n is an integer from 10–450. The molecular mass of the inventive compounds ranges from 700–30,000, as determined by the vapor pressure method. The inventive compounds may be prepared by reacting 0(2,6-dichlorophenylamino) phenylacetic acid with polyethyleneglycols having the formula HO (CH$_2$—CHO$_2$)$_n$H, where n is as defined above, in the presence of an acid and while heated in an inactive solvent. The inventive compounds exhibit a high antiphlogistic activity, but are much less irritating to the stomach mucosa then the prior art compounds.

3 Claims, No Drawings

ESTERS OF O(2,6-DICHLOROPHENYLAMINO) PHENYLACETIC ACID

This invention relates to biologically active esters of O(2,6-dichlorophenylamino) phenylacetic acid and a method for their preparation.

BACKGROUND OF THE INVENTION

A sodium salt of O(2,6-dichlorophenylamino) phenylacetic acid, Feloran TM, is known. This compound exhibits a useful antiphlogistic and antirheumatic action, but is irritating to the stomach mucosa. See, *Clinical Pharmacology and Therapeutics,* Vol. 26, No. 3, Pages 339-405 (St. Luis: 1979); C.A. Winter et al, *Proc. Soc. Exp. Biol. Med.,* Vol. 11, Pages 544-547 (1962); J.R. Parrat et al, *J. Physiol.,* Vol 139, Pages 24-41 (London: 1957); and Domenjcz, *Actualites Pharmacol.,* Vol. 7, Pages 8-12, (Paris: 1954).

SUMMARY OF THE INVENTION

It is an object of the present invention to provide new synthetic esters of O(2,6-dichlorophenylamino) phenylacetic acid which have an antiphlogistic action but which do not irritate the stomach mucosa.

The compounds, according to the invention, are esters of O (2,6-dichlorophenylamino) phenylacetic acid with polyethyleneglycols. These compounds have the following formula:

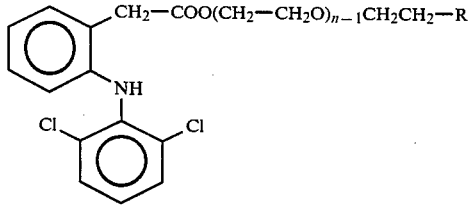

wherein R represents a hydroxyl group or the group

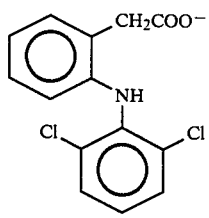

and n is an integer from 10-450, with a molecular mass of from 700-30,000, determined according to the vapor pressure method.

The method of preparing these compounds, according to the invention, comprises the interaction of O(2,6-dichlorophenylamino) phenylacetic acid having the general formula

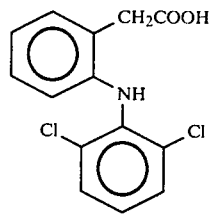

with polyethyleneglycols having the general formula $HO(CH_2CH_2O)_nH$, in which n is an integer from 10-450, in an inactive solvent (such as aromatic hydrocarbons, including benzene and toluene, or chlorinated hydrocarbons, including tetrachloromethane) in the presence of catalytic amounts of acid, such as chlorosulphonic acid or p-toluene sulphonic acid, under heating; with azeotropic separation of water or in the presence of a molecular sieve. After termination of the reaction and neutralization of the solution, the product is isolated by reprecipitation with diethyl ether.

The present compounds are advantageous because they exhibit the same antiphlogistic effect as the known compound, but are much less irritating to the stomach mucosa.

The inventive compounds and their preparation are further described by reference to the following examples. It will be understood by those skilled in the art that these examples are illustrative only and do not serve to limit the scope of the invention or the appended claims.

EXAMPLE 1

A suspension of 1.48 g (0.005 moles) of O(2,6-dichlorophenylamino) phenylacetic acid in 20 ml of benzene is prepared. A solution containing 3.37 g (0.0025 moles) of polyethyleneglycols dissolved in 20 ml benzene and containing 0.05 g p-toluene sulphonic acid is also prepared. The solution is added to he suspension, and the resulting mixture is stirred and heated at 60° C. for 10 hours, in the presence of a molecule sieve. After completion of the reaction, benzene is distilled in vacuum, 30 ml of chloroform are added, and the chloroform solution is washed with a 0.1 N solution of NaOH (2.25 ml) and with water (2.25 ml). The solution is then dried with $Na_2SO_4$ and then chloroform is distilled in vacuum. The product obtained is purified by benzene-diethylene ether (1:1), is left to crystallize at 10° C., and is then is filtered and washed with diethylether.

The yield is 4.3 g (90% of the theoretical value) of the inventive compound

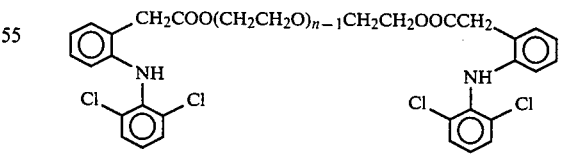

The infrared spectrum had a band ($\gamma$-COO—) at 1720 $cm^{-1}$. The ultra-violet spectrum in ethanol ($-\lambda_{max}$) is 280 nm. The average numeric molecular mass is 1900, determined by the vapor pressure method.

The inventive compound wherein R is a hydroxyl group is prepared by a similar method, but the amount of polyethyleneglycols with average molecular mass of 1350 is 6.75 g (0.005 moles). The actual yield of this compound is 7.3 g (88% of the theoretical value). The IR spectrum has a specfific band ((Ⓒ-COO) at 1720 cm$^{-1}$ and ((Ⓒ-OH) is at 3500 cm$^{-1}$. The UV spectrum in ethanol ($-\#_{max}$) is 280 nm. The average numeric molecular mass is 1600.

EXAMPLE 2

The preparation of inventive compounds having an average molecular mass of 10600 (when R is the complex radical defined above) and a molecular mass of 10300 (when R is a hydroxyl group) is similar to he method described in Example 1, but the amount of polyethyleneglycols having an average molecular mass of 10,000 is 25 g and 50 g, respectively. The actual yields of product in both cases is 80% of the theoretical yield. The lighter compounds (R=OH) have an IR peak ((Ⓒ-COO) at 1720 cm$^{-1}$ and ((Ⓒ-OH) at 3500 cm$^{-1}$. The heavier compounds have an IR peak ((Ⓒ-COO) at 1720 cm$^{-1}$. Both compounds have an ultraviolet spectrum in ethanol ($-\#_{max}$) at 280 nm.

EXAMPLE 3

Polyethylene glycol bis 0(2,6-dichlorophenylamino) phenylacetate

The diester of 0(2,6-dichlorophenylamino) phenylacetic acid with polyethyleneglycols having an average molecular mass of 1350 [p(M$_w$)M$_n$-1.15] and n is about 30 (R is the complex radical) has been compared with the known compound Feloran TM. Both compounds were administered per os to "Vistar" rats to determine antiphlogistic activity and the tendency of both compounds to irritate the stomach mucosa. Three groups of white "Vistar"rats, with 10 rats per group, were treated to create an inflammation model. One group was treated with caragenine, according to the method of Winter et al. *Broc. Soc. Exp. Biol. Med.*, Vol. 111, Pages 544–547 (1962). A second group was treated with dextrane according to the method of Parrat et al, *J. Physiol.*, Vol. 139, Pages 24–41 (London: 1957). A third group was treated with formalin, according to the method of Domenjcz, *Actualites Pharmacol.*, Vol. 7, Pages 8–12, (Paris: 1954). Each group of laboratory rats, was dosed with from 2.5 to 3 mg/kg, per os, of the inventive diester. Another series theories of trials with artificially inflamed rats was dosed in the same manner with the same amount of Feloran TM. It was determined that the antiphlogistic activity in the experimental trials corresponding to the inventive diester is the same as the antiphlogistic activity observed in the Feloran TM control.

White "Vistar" rats, in groups of six, were tested to determine the extent to which an inventive diester of 0(2,6-dichlorophenylamino) phenylacetic acid with polyethyleneglycols, having an average molecular mass of 1350 (R is the complex radical) irritates the stomach mucosa, in comparison with the known compound. The rats were dosed with from 8-10 mg/kg of the inventive and known compounds. At a dose of 8 mg/kg, the inventive diester caused hemorrhages in the stomach mucosa of only one animal, while all six animals treated with Feloran TM developed microscopic ulcers. At a dose of 10 mg/kg, three of the animals treated with the inventive diester developed small ulcers, whereas all six animals treated with the known compound developed large ulcers.

The comparative pharmacological studies indicate that the inventive diester having an average molecular mass of 1350 exhibits the same antiphlogistic activity as the known compound when administered to rats per os, but is only half as irritating to the stomach mucosa.

We claim:

1. Esters of 0(2,6-dichlorophenylamino) phenylacetic acid with polyethyleneglycols having the formula:

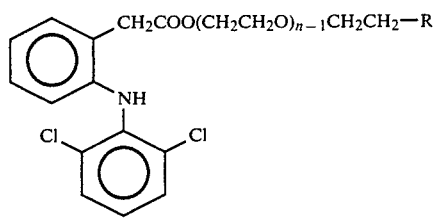

wherein R is selected from the group consisting of a hydroxyl group and the group

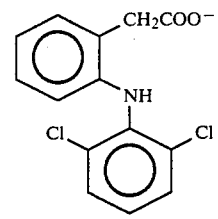

and n is an integer from 10–450.

2. An ester of 0(2,6-dichlorophenylamino) phenylacetic acid with polyethyleneglycols having the formula

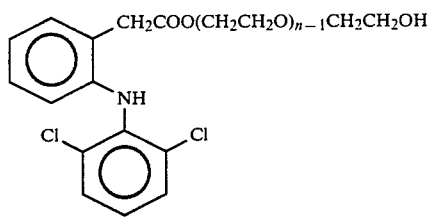

where n is an integer from 10–450.

3. An ester of 0(2,6-dichlorophenylamino) phenylacetic acid with polyethyleneglycols having the formula

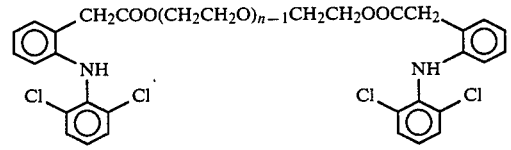

where n is an integer from 10–450.

* * * * *